(12) United States Patent
Hasser et al.

(10) Patent No.: US 10,646,293 B2
(45) Date of Patent: May 12, 2020

(54) LAPAROSCOPIC ULTRASOUND ROBOTIC SURGICAL SYSTEM

(71) Applicants: Intuitive Surgical Operations, Inc., Sunnyvale, CA (US); The Johns Hopkins University, Baltimore, MD (US)

(72) Inventors: Christopher J. Hasser, Los Altos, CA (US); Russell H. Taylor, Severna Park, MD (US); Joshua Leven, San Francisco, CA (US); Michael Choti, Lutherville, MD (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 577 days.

(21) Appl. No.: 15/413,380

(22) Filed: Jan. 23, 2017

(65) Prior Publication Data
US 2017/0128041 A1    May 11, 2017

Related U.S. Application Data

(62) Division of application No. 11/447,668, filed on Jun. 6, 2006.
(Continued)

(51) Int. Cl.
*A61B 1/00*    (2006.01)
*A61B 34/37*   (2016.01)
(Continued)

(52) U.S. Cl.
CPC ............ *A61B 34/37* (2016.02); *A61B 1/3132* (2013.01); *A61B 8/12* (2013.01); *A61B 8/4218* (2013.01);
(Continued)

(58) Field of Classification Search
CPC .......... A61B 34/37; A61B 34/25; A61B 34/76
(Continued)

(56) References Cited

U.S. PATENT DOCUMENTS

| 4,672,963 A | 6/1987 | Barken |
| 5,279,309 A | 1/1994 | Taylor et al. |

(Continued)

FOREIGN PATENT DOCUMENTS

| EP | 514584 A2 | 11/1992 |
| EP | 0732082 B1 | 9/2002 |

(Continued)

OTHER PUBLICATIONS

Office Action dated Feb. 13, 2015 for Japanese Application No. 20140086093 filed Apr. 18, 2014, 1 page.
(Continued)

*Primary Examiner* — Matthew J Kasztejna

(57) ABSTRACT

A LUS robotic surgical system is trainable by a surgeon to automatically move a LUS probe in a desired fashion upon command so that the surgeon does not have to do so manually during a minimally invasive surgical procedure. A sequence of 2D ultrasound image slices captured by the LUS probe according to stored instructions are processable into a 3D ultrasound computer model of an anatomic structure, which may be displayed as a 3D or 2D overlay to a camera view or in a PIP as selected by the surgeon or programmed to assist the surgeon in inspecting an anatomic structure for abnormalities. Virtual fixtures are definable so as to assist the surgeon in accurately guiding a tool to a target on the displayed ultrasound image.

16 Claims, 8 Drawing Sheets

Related U.S. Application Data

(60) Provisional application No. 60/688,013, filed on Jun. 6, 2005.

(51) Int. Cl.

| | | |
|---|---|---|
| *A61B 8/00* | (2006.01) | |
| *A61B 34/00* | (2016.01) | |
| *A61B 90/00* | (2016.01) | |
| *A61B 8/12* | (2006.01) | |
| *A61B 34/30* | (2016.01) | |
| *A61B 1/313* | (2006.01) | |
| *A61B 34/10* | (2016.01) | |
| *A61B 17/00* | (2006.01) | |

(52) U.S. Cl.
CPC ............ *A61B 8/4245* (2013.01); *A61B 8/461* (2013.01); *A61B 34/25* (2016.02); *A61B 34/30* (2016.02); *A61B 34/70* (2016.02); *A61B 34/76* (2016.02); *A61B 90/361* (2016.02); *A61B 90/37* (2016.02); *A61B 8/00* (2013.01); *A61B 90/03* (2016.02); *A61B 2017/00203* (2013.01); *A61B 2034/107* (2016.02); *A61B 2034/305* (2016.02); *A61B 2090/364* (2016.02); *A61B 2090/365* (2016.02); *A61B 2090/378* (2016.02)

(58) Field of Classification Search
USPC ................................ 600/101, 111, 116, 166; 348/211.1–211.4
See application file for complete search history.

(56) References Cited

U.S. PATENT DOCUMENTS

| | | |
|---|---|---|
| 5,397,323 A | 3/1995 | Taylor et al. |
| 5,408,409 A | 4/1995 | Glassman et al. |
| 5,417,210 A | 5/1995 | Funda et al. |
| 5,482,029 A | 1/1996 | Sekiguchi et al. |
| 5,493,595 A | 2/1996 | Schoolman |
| 5,551,432 A | 9/1996 | Iezzi |
| 5,572,999 A | 11/1996 | Funda et al. |
| 5,601,549 A | 2/1997 | Miyagi |
| 5,749,362 A | 5/1998 | Funda et al. |
| 5,759,153 A | 6/1998 | Webler et al. |
| 5,765,561 A | 6/1998 | Chen et al. |
| 5,788,688 A | 8/1998 | Bauer et al. |
| 5,797,849 A | 8/1998 | Vesely et al. |
| 5,797,900 A | 8/1998 | Madhani et al. |
| 5,810,008 A | 9/1998 | Dekel et al. |
| 5,817,022 A | 10/1998 | Vesely |
| 5,836,880 A | 11/1998 | Pratt |
| 5,842,473 A | 12/1998 | Fenster et al. |
| 5,842,993 A | 12/1998 | Eichelberger et al. |
| 5,853,367 A | 12/1998 | Chalek et al. |
| 5,876,325 A | 3/1999 | Mizuno et al. |
| 5,887,121 A | 3/1999 | Funda et al. |
| 6,129,670 A | 10/2000 | Burdette et al. |
| 6,201,984 B1 | 3/2001 | Funda et al. |
| 6,226,566 B1 | 5/2001 | Funda et al. |
| 6,241,725 B1 | 6/2001 | Cosman |
| 6,256,529 B1 | 7/2001 | Holupka et al. |
| 6,402,737 B1 | 6/2002 | Tajima et al. |
| 6,425,865 B1 | 7/2002 | Salcudean et al. |
| 6,440,072 B1 | 8/2002 | Schuman et al. |
| 6,459,926 B1 | 10/2002 | Nowlin et al. |
| 6,468,212 B1 | 10/2002 | Scott et al. |
| 6,493,608 B1 | 12/2002 | Niemeyer |
| 6,522,906 B1 | 2/2003 | Salisbury, Jr. et al. |
| 6,547,782 B1 | 4/2003 | Taylor |
| 6,599,247 B1 | 7/2003 | Stetten |
| 6,602,185 B1 | 8/2003 | Uchikubo |
| 6,642,836 B1 | 11/2003 | Wang et al. |
| 6,659,939 B2 | 12/2003 | Moll et al. |
| 6,714,839 B2 | 3/2004 | Salisbury et al. |
| 6,799,065 B1 | 9/2004 | Niemeyer |
| 6,819,785 B1 | 11/2004 | Vining et al. |
| 6,837,883 B2 | 1/2005 | Moll et al. |
| 7,107,090 B2 | 9/2006 | Salisbury et al. |
| 7,107,124 B2 | 9/2006 | Green |
| 7,144,367 B2 | 12/2006 | Chen et al. |
| 7,155,042 B1 | 12/2006 | Cowan et al. |
| 7,155,316 B2 | 12/2006 | Sutherland et al. |
| 7,413,565 B2 | 8/2008 | Wang et al. |
| 8,155,479 B2 | 4/2012 | Hoffman et al. |
| 8,398,541 B2 | 3/2013 | Dimaio et al. |
| 9,603,508 B2 | 3/2017 | Hale et al. |
| 9,795,446 B2 | 10/2017 | Dimaio et al. |
| 2001/0037064 A1 | 11/2001 | Shahidi |
| 2002/0193800 A1 | 12/2002 | Kienzle, III |
| 2004/0143181 A1 | 7/2004 | Damasco et al. |
| 2004/0201752 A1 | 10/2004 | Parulski et al. |
| 2005/0085718 A1 | 4/2005 | Shahidi |
| 2005/0187472 A1 | 8/2005 | Lysyansky et al. |
| 2005/0267359 A1 | 12/2005 | Hussaini et al. |
| 2005/0281444 A1 | 12/2005 | Lundberg et al. |
| 2006/0041180 A1 | 2/2006 | Viswanathan et al. |
| 2006/0058988 A1 | 3/2006 | Defranoux et al. |
| 2006/0258938 A1 | 11/2006 | Hoffman et al. |
| 2007/0021738 A1 | 1/2007 | Hasser et al. |
| 2013/0245375 A1 | 9/2013 | Dimaio et al. |
| 2017/0128144 A1 | 5/2017 | Hasser et al. |
| 2017/0128145 A1 | 5/2017 | Hasser et al. |
| 2018/0042680 A1 | 2/2018 | Dimaio et al. |

FOREIGN PATENT DOCUMENTS

| | | |
|---|---|---|
| EP | 1310844 A1 | 5/2003 |
| EP | 1424173 A2 | 6/2004 |
| JP | H06110543 A | 4/1994 |
| JP | H07184923 A | 7/1995 |
| JP | H0819975 A | 1/1996 |
| JP | H08299363 A | 11/1996 |
| JP | H10146341 A | 6/1998 |
| JP | 2000500679 A | 1/2000 |
| JP | 2001000448 A | 1/2001 |
| JP | 2002287613 A | 10/2002 |
| JP | 2003053684 A | 2/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005303327 A | 10/2005 |
| JP | 2005334650 A | 12/2005 |
| WO | WO-2005039391 A2 | 5/2005 |
| WO | WO-2005043319 A2 | 5/2005 |

OTHER PUBLICATIONS

Rasmussen, Christopher et al., "Joint Probabilistic Techniques for Tracking Multi-Part Objects," Computer Vision and Pattern Recognition, 1998. Proceedings. 1998 IEEE Computer Society Conference on Jun. 23-25, 1998, pp. 16-21.
3D Slicer web site,http//www.slicer.org,2003.
Abolmaesumi, Purang et al., "A User Interface for Robot-Assisted Diagnostic Ultrasound," IEEE Robotics and Automation Conference, 2001, pp. 1549-1554, vol. 2, IEEE.
Abolmaesumi, Purang et al., "Image Guided Control of a Robot for Medical Ultrasound," IEEE Transactions on Robotics and Automation, 2002, pp. 11-23, vol. 18—Issue 1, IEEE.
Ahlering, Thomas. E. et al., "Robotic radical prostatectomy: a technique to reduce pT2 positive margins," Urology, 2004, pp. 1224-1228, vol. 64 Issue 6, Elsevier Inc.
Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.
Azuma, Ronald T., "A Survey of Augmented Reality," Teleoperators and Virtual Environments, 1997, pp. 355-385, vol. 6—No. 4.
Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

(56) References Cited

OTHER PUBLICATIONS

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total, Morgan kaufmann publishers, Inc.

Bartels, Richard H. et al., "Solution of the Matrix Equation AX+XB=C," Communications of the ACM, 1972, pp. 820-826, vol. 15—Issue 9, ACM Press.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

Boctor, Emad, M. et al., "CISUS: An integrated 3D ultrasound system for IGT using a modular tracking API," Proceedings of the SPIE, 2004, pp. 247-256, vol. 5367, SPIE.

Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.

Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science, 2001, pp. 13-22, vol. 2074, Springer.

Boctor, Emad, M. et al., "Robot-assisted 3D strain imaging for monitoring thermal ablation of liver," Annual congress of the Society of American Gastrointestinal Endoscopic Surgeons (SAGES), Emerging Technology Lunch Poster TP004, 2005, pp. 240-241.

Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.

Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.

Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, Spie. 0.

Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.

Brown, Myron M. et al., "Advances in Computational Stereo," IEEE Transactions on Pattern Analysis and Machine Intelligence (PAMI), 2003, pp. 993-1008, vol. 25 Issue, IEEE.

Burschka, Darius et al., "Scale-Invariant Registration of Monocular Endoscopic Images to CT-Scans for Sinus Surgery," Med Image Anal, 2004, pp. 413-421, vol. 2, Springer-Verlag.

Burschka, Darius et al., "Scale-Invariant Registration of Monocular Stereo Images to 3D Surface Models," IEEE Int. Conf. on Robots and Systems, 2004, pp. 2581-2586, vol. 3, IEEE.

Burschka, Darius et al., "Navigating Inner Space: 3-D Assistance for Minimally Invasive Surgery," Robotics and Autonomous Systems, 2005, pp. 5-26, vol. 52—Issue 1, Elsevier.

Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.

Bzostek, Andrew, "Computer-Integrated needle therapy systems: Implementation and Analysis," Computer Science, 2005, 379 pages.

Bzostek, Andrew et al., "A Testbed System for Robotically Assisted Percutaneous Pattern Therapy," Medical Image Computing and Computer-Assisted Surgery, Lecture Notes In Computer Science, 1999, pp. 1098-1107, vol. 1679, Springer.

Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.

Bzostek, Andrew, "Image Guided Percutaneous Pattern Placement in Soft Tissue," The Johns Hopkins University Dept. of Computer Science: Baltimore, 1997, pp. 2007-01-22.

Cadeddu, Jeffrey A. et al., "A Robotic System for Percutaneous Renal Access," The Journal of Urology, 1997, pp. 1589-1593, vol. 158—Issue 4.

Cadeddu, Jeffrey et al., "A robotic system for percutaneous renal access incorporating a remote center of motion design," Journal of Endourolog, 1998, S237, vol. 12.

Cannon, Jeremy W. et al., "Real-time three-dimensional ultrasound for guiding surgical tasks," Computer Aided Surgery, 2003, pp. 82-90, vol. 8—No. 2, John Wiley & Sons.

Carr, J., "Surface reconstruction in 3D medical imaging," PhD Thesis, University of Canterbury, Christchurch, New Zealand, 1996, 223 Pages.

Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.

Chang, Jun Keun et al., "Intravascular micro active catheter for minimal invasive surgery," 1st Annual International Conference on Microtechnologies in Medicine and Biology, 2000, pp. 243-246.

Chen, Homer H. "A Screw Motion Approach to Uniqueness Analysis of Head-Eye Geometry," Computer Vision and Pattern Recognition, 1991, pp. 145-151, IEEE.

(56) References Cited

OTHER PUBLICATIONS

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the Art in Surgical Robotics:Clinical Applications and Technology Challenges," Computer Aided Surgery, 2001 [retrieved on Feb. 24, 2002], pp. 1-26 .
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Degoulange, E. et al., "HIPPOCRATE: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, pp. 4.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Extended European Search Report for Application No. 11150207.6, dated Jan. 12, 2015, 6 pages.
Extended European Search Report for Application No. EP11150208, dated Feb. 17, 2014, 5 pages.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Frantz D.D et al., "Accuracy assessment protocols for electromagnetic tracking systems," Physics in Medicine and Biology, 2003, pp. 2241-2251, Issue 48.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Funda, Janez, "An experimental user interface for an interactive surgical robot," In 1st International Symposium on Medical Robotics and Computer Assisted Surgery (MRCAS 94), Pittsburgh, 1994, pp. 196-201, 203.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, Arthur et al., "Applied Optimal Estimation," 1974, 4 Pages Total.
Gennari, G. et al., "Probabilistic data association methods in visual tracking of groups," IEEE Conference on Computer Vision and Pattern Recognition, 2004, pp. I-790-1-797, vol .1—issue. 27, IEEE.
Gigot, Jean-Francois et al., "Laparoscopic Liver Resection for Malignant Liver Tumors Prclimary Results of a Multicenter European Study," Ann Surg, 2002, pp. 90-7, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.

(56) References Cited

OTHER PUBLICATIONS

Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.
Hager, Gregory D. et al., "The XVision System: A Portable Substrate for Real Time Vision Applications," 1998, pp. 23-37, vol. 69—issue 1.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline, Alan J. et al., "Image-Guided Surgery: Preliminary Feasibility Studies of Frameless Stereotactic Liver Surgery," Archives of Surgery, 1999, pp. 644-650, vol. 134—No. 6.
Herline, Alan J. et al., "Surface Registration for Use in Interactive," Image-Guided Liver Surgery, Computer Aided Surgery, 2000, pp. 11-17, vol. 5—No. 2.
Herman, Barry C., et al, "Telerobotic surgery creates opportunity for augmented reality surgery," Abstract No. T1F2, Telemedicine Journal and E-Health, vol. 11, Issue 2, p. 203, Apr. 2005.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Hespanha J.P. et al., "What Tasks Can Be Performed with an Uncalibrated Stereo Vision System", International Journal of Computer Vision, 1999, pp. 65-85, vol. 35—issue. (1).
Ho, S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Intuitive Surgical, Inc., "Intuitive Surgical daVinci API v5.0 Reference Manual," generated Jul. 17, 2006, 149 pages.
Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Johns Hopkins University and Intuitive Surgical, Inc., "System Requirements for the Surgical Assistant Workstation," Rev. 2, Jan. 29, 2007, 17 pages.
Joskowicz, Leo et al., "Computers in Imaging and Guided Surgery," Computing in Science and Engineering, 2001, pp. 65-72, vol. 3—Issue: 5, IEEE.
Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.
Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.
Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.
Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI,, Lecture Notes in Computer Science, 2003, vol. 1, Springer.
Kapoor, Ankur et al., "Suturing in Confined Spaces: Constrained Motion Control of a Hybrid 8—DOF Robot," Proceedings, 12th International Conference on Advanced Robotics, 2005, pp. 452-459.
Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.
Kavoussi, Louis R., "Laparoscopic donor nephrectomy," Kidney International, 2000, pp. 2175-2186, vol. 57.
Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H. , "Human Extenders," ASME J. Dynamic Systems, Measurements and Control, 1993, pp. 281-290, vol. 115 No. 2(B).
Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kragic D. et al., "Human-Machine Collaborative Systems for Microsurgical Applications," International Symposium on Robotics Research, 2005, pp. 731-741, vol. 24—Issue 9, Sage Publications.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.
Kumar, Rajesh, "An Augmented Steady Hand System for Precise Micromanipulation," 2001, 109 pages.

(56) References Cited

OTHER PUBLICATIONS

Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.

Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.

Kumar, Rajesh et al., "Experiments with a Steady Hand Robot in Constrained Compliant Motion and Path Following", 1999, pp. 92-97, IEEE.

Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.

Kumar, Rajesh et al., "Preliminary experiments in robot/human microinjection," IEEE/RSJ International Conference on Intelligent Robots and Systems, 2003, pp. 3186-3191, vol. 3, IEEE.

Lacroute, Philippe et al., "The VolPack Volume Rendering Library," 2003, pp. 4.

Lacroute, Philippe G., "Fast Volume Rendering Using a Shear-Warp Factorization of the Viewing Transformation PhD Thesis," Computer Science, Stanford, California, 1995, 236 Pages.

Lang, Samuel J., Xvision 2—A Framework for Dynamic Vision. Masters Thesis, Computer Science, Johns Hopkins University, Baltimore, 2001, pp. 1-49.

Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.

Lau, William W. et al., "Stereo-Based Endoscopic Tracking of Cardiac Surface Deformation," Proceedings of Seventh International Conference on Medical Image Computing and Computer—Assisted Intervention (MICCAI), Lecture Notes in Computer Science, 2004, pp. 494-501, vol. 2, Springer Verlag.

Lavonius, Maija I. et al., "Staging of Gastric Cancer: A Study with Spiral Computed Tomography, Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

Lawson, Charles L. et al., "Linear least squares with linear inequality constraints Solving Least Squares Problems," 1974, pp. 158-173, Prentice Hall Inc.

Lee Jr, Fred T. et al., "CT-monitored percutaneous cryoablation in a pig liver model," Radiology, 1999, pp. 687-692, vol. 211(3).

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—Iss. 3, IEEE.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures, IEEE," HAPTICS 2003, 11th Symposium on Haptic Interfaces for Virtual Environment and Teleoperator Systems, Mar. 22-23, 2003, pp. 125-131, IEEE.

Li, Ming, "Intelligent Robotic Surgical Assistance for Sinus Surgery," Ph.D. Dissertation, Computer Science, Johns Hopkins University, Baltimore, 2005, 229 pages.

Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-81, vol. 3976, SPIE.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and

(56) References Cited

OTHER PUBLICATIONS

Computer-Assisted Intervention, Lecture Notes in Computer Science, 2001, pp. 343-350, vol. 2208, Springer-Verlag.
Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.
Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.
Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.
Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.
Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.
Nakakura, Eric K et al., "Hepatocellular Carcinoma: Current Management Recommendations," Advances on Oncology, 2000, pp. 12-18, vol. 16—No. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Novotny Paul M. et al., "Tool Localization in 3D Ultrasound Images," Medical Image Computing and Computer-Assisted Intervention, 2003, pp. 969-970, vol. 2879, Springer.
Office Action dated Jan. 5, 2009 for European Application No. 20060784595 filed Jun. 5, 2006, 2 pages.
Office Action dated Jan. 12, 2012 for Japanese Application No. 20080515812 filed Jun. 5, 2005, 5 pages.
Office Action dated Mar. 16, 2015 for Japanese Application No. 20110272384 filed Dec. 13, 2011, 22 pages.
Office Action dated Jun. 19, 2014 for Japanese Application No. 20110272384 filed Dec. 13, 2011, 3 pages.
Office Action dated Nov. 19, 2013 for Chinese Application No. 2006820112 filed Jun. 5, 2006, 9 pages.
Office Action dated Jun. 20, 2013 for Japanese Application No. 20110272385 filed Dec. 13, 2011, 5 pages.
Office Action dated Jun. 20, 2013 for Japanese Application No. 20110272386 filed Dec. 13, 2011, 8 pages.
Office Action dated Jun. 20, 2013 for Japanese Application No. JP20110272384 filed Dec. 13, 2011, 7 pages.
Office Action dated Dec. 27, 2013 for Japanese Application No. 20110272384 filed Dec. 13, 2011, 5 pages.
Office Action dated Dec. 27, 2013 for Japanese Application No. 20110272386 filed Dec. 13, 2011, 8 pages.
Office Action dated Feb. 27, 2015 for Japanese Application No. 20130194017 filed Sep. 19, 2013, 4 pages.
Office Action dated Aug. 28, 2015 for Japanese Application No. 20140086093, filed Apr. 18, 2014, 3 page.
Office Action dated Aug. 31, 2011 for Japanese Application No. 20080515812 filed Jun. 5, 2005, 10 pages.
Office Action dated Jul. 31, 2014 for Japanese Application No. 2013-194017 filed Sep. 19, 2013.
Ohbuchi, Ryutarou et al., "Incremental Volume Reconstruction and Rendering for 3D Ultrasound Imaging," The International Society of Optical Engineering, 1992, pp. 312-323, vol. 1808, SPIE.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu Alexandru et al., "Motion-based robotic instrument targeting under c-arm fluoroscopy," Medical Image Computing and Computer-Assisted Interventions, 2000, pp. 988-998, vol. 1935, Springer.
PCT/US06/21852 International Search Report dated Nov. 2, 2006, 3 pages.
PCT/US06/21852 Written Opinion of the International Search Authority dated Nov. 2, 2006, 6 pages.
PCT/US06/40754 International Search Report dated Jul. 11, 2007, 4 pages.
PCT/US06/40754 Written Opinion of the International Search Authority dated Apr. 23, 2008, 8 pages.
Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.
Poulose P. K et al., "Human vs Robotic Organ Retraction During Laparoscopic Nissen Fundoplication," Surgical Endoscopy, 1999, pp. 461-465, vol. 13, Springer-Verlag.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad, Srinivas K. et al., "A minimally invasive approach to pelvic osteolysis," 2002, in Proc. Computer-Assisted Orthopaedic Surgery (CAOS), pp. 349-350.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Ramey, Nicholas A., "Stereo-Based Direct Surface Tracking with Deformable Parametric Models," 2003, 104 Pages Total.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al, "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging," Digestive Surgery, 2002, pp. 479-483, vol. 19—No. 6.
Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.
Rohling, Robert et al., "Three-dimensional spatial compounding of ultrasound images," Medical Image Analysis, 1996, pp. 177-193, vol. 1—No. 3, Oxford University Press.

(56) References Cited

OTHER PUBLICATIONS

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radiofrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

Solomon, Stephen B. et al., "CT Guided Robotic Needle Biopsy: A Precise Sampling Method Minimizing Radiation Exposure to the Physician, Radiology," 2002, pp. 277-282, vol. 225.

Solomon, Stephen B. et al., "Robotically Driven Interventions: A Method of Using CT Fluoroscopy without Radiation Exposure to the Physician," Radiology, 2002, pp. 277-282, vol. 225.

Solus-3D web site: Last updated Jun. 24, 1999; downloaded Jul. 5, 2007.

Sommer, Graham et al., "Liver tumors: utility of characterization at dual frequency US," Radiology, 1999, pp. 629-636, vol. 211—No. 3.

Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.

Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.

Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoainovici D., et al., "Robotic Telemanipulation for Percutaneous Renal Access," in 16th World Congress on Endourology, New York City, Sep. 3-6, 1998, Poster Session 17-5, p. S201.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

Stoianovici, Dan et al., "Robotic for Precise Percutaneous Needle Insertion," In Thirteenth Annual Meeting of the Society for Urology and Engineering. San Diego, May 1998, pp. 4.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA .

Taylor, Russell H., "A Perspective on Medical Robotics," Proceedings of the IEEE, vol. 94, No. 9, Sep. 2006, pp. 1652-1664.

Taylor, Russell H. "An Image-directed Robotic System for Precise Orthopaedic Surgery," IEEE Transactions on Robotics mid Automation, 1994, pp. 261-275, vol. 10—No. 3, IEEE.

Taylor, Russell H. and Christopher Hasser, "Development of a Surgical Assistant Workstation for Teleoperated Surgical Robots," NSF Proposal No. 0646678, Aug. 2006, 16 pages.

Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.

Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.

Taylor, Russell H. et al., "A Computational Architecture for Programmable Automation Research," Conference on Intelligent Robots and Computer Vision, 1986, pp. 438-440, vol. 726, SPIE.

(56) References Cited

OTHER PUBLICATIONS

Taylor, Russell H. et al., "A General Purpose Control Architecture for Programmable Automation Research," Proceedings of the Third International Symposium on Robotics, 1986, pp. 165-174, MIT Press.

Taylor, Russell, H et al., "A Steady-Hand Robotic System for Microsurgical Augmentation," International Journal of Robotics Research, 1999, pp. 1201-1210, vol. 18—No. 12, Springer-Verlag.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.

Taylor, Russell, H et al., "AML a Manufacturing Language," The International Journal of Robotics Research, 1982, pp. 19-41, vol. 1—No. 3, SAGE Publications.

Taylor, Russell H. et al., "An Image-directed Robotic System for Hip Replacement Surgery," J. Robotics Society of Japan, 1990, pp. 615-620, vol. 8—issue 5.

Taylor, Russell, H. et al., "An Integrated Robot Systems Architecture," Proceedings of the IEEE, 1983, pp. 842-856, vol. 71—Issue 7, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.

Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.

Taylor, Russell H. et al., "Computer-Integrated Surgery," 1996, 8 Pages, MIT Press.

Taylor, Russell H. et al., "Medical Robotics and Computer-Integrated Surgery," Chapter 52 in Springer Handbook of Robotics, Springer, 2008, pp. 1199-1222.

Taylor, Russell H. et al., "Medical Robotics in Computer-Integrated Surgery," IEEE Transactions on Robotics and Automation, 2003, pp. 765-781, vol. 19—No. 5, IEEE.

Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.

Taylor, Russell, H et al., "The Architecture of an Integrated Robot System," First Int. Conf. on Advanced Robotics (ICAR)., 1983, pp. 389-398.

Taylor, Russell H. "Medical Robotics and Computer-Integrated Surgery," Handbook of Industrial Robotics, Second Edition, 1999, pp. 1213-1230, Chapter 65, John Wiley & Sons.

Taylor, Russell H. "Medical Robots," in Computer and Robotic Assisted Knee and Hip Surgery, 2004, pp. 54-59, Oxford Press.

Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.

Taylor, Russell H. "The Planning and Execution of Straight Line Manipulator Trajectories," IBM Journal of Research and Development, 1979, pp. 424-436, vol. 23—Issue 4.

Taylor, Russell H., "Ultrasound Assistant for a Laparoscopic Surgical Robot," NIH STTR Phase II Proposal R42-RR019159, revised May 2001, 54 pages.

Taylor, Russell H., Videotape: "Computer Assisted Surgery at IBM T. J. Watson Research Center," 22 minutes 10 seconds, 1994 and 1995.

Teistler, Michael et al., "Virtual Tomography: A New Approach to Efficient Human-Computer Interaction for Medical Imaging, Proc. of SPIE,," The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.

Tewari, Ashutosh et al., "Technique of da Vinci Robot-Assisted Anatomic Radical Prostatectomy," Urology, 2002, pp. 569-572,vol. 60—No. 4, Elsevier.

Toyama, Kentaro et al., "Incremental Focus of Attention for Robust Visual Tracking," International Journal of Computer Vision, 1999, pp. 45-63, vol. 35—No. 1, Kluwer Academic Publishers.

Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.

Uecker, Darrin R. et al., "A Speech-Directed Multi-Modal Man-Machine Interface for Robotically Enhanced Surgery," 1994, pp. 176-183.

Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.

U.S. Appl. No. 11/583,963 Non-Final Office Action dated Jul. 9, 2009, 40 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Vilchis, Adriana et al., "A New Robot Architecture for Tele-Echography," IEEE Trans. Robotics & Automation, pp. 922-926, 2003, vol. 19—No. 5, IEEE.

Viswanathan, Anand et al., "Immediate Ultrasound Calibration with Three Poses and Minimal Image Processing," MICCAI, 2004, pp. 446-454, vol. 2, Springer-Verlag.

Webster Robert J. et al., "Design Considerations for Robotic Needle Steering," International Conference on Robotics and Automation, 2005, pp. 3588-3594, IEEE.

Webster Robert J. et al "Nonholonomic Modeling of Needle Steering," The International Journal of Robotics Research, 2004, pp. 509-525, vol. 25—No. 5-6, SAGE Publications.

Wei, Zhouping et al "Robot-assisted 3D-TRUS guided prostate brachytherapy: system integration and validation," Medical Physics, 2004, pp. 539-548, vol. 31—No. 3.

Wengert, Christian, "Camera Calibration Toolbox for Matlab," [online][retrieved on Oct. 24, 2006], Retrieved from the Internet:< url:>, 5 pages.<url:></url:></url:>.

Wilhelm, Dirk et al., "Electromagnetically Navigated Laparoscopic Ultrasound," Surg. Technol. Int, 2003, pp. 50-54, vol. 11.

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," International Society of Optical Engineering, 2004, pp. 394-402, SPIE.

Yamagata, Hitoshi, "Development of a New Display Method for Compound 3D Ultrasound Images: Fusion 3D Images From B-mode and 3D Doppler Images," 1999, pp. 43-46, vol. 70.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

(56) References Cited

OTHER PUBLICATIONS

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Zhengyou, "A Flexible New Technique for Camera Calibration," 1998, pp. 1-21.

LAPAROSCOPIC ULTRASOUND ROBOTIC SURGICAL SYSTEM

CROSS REFERENCE TO RELATED APPLICATIONS

This application is a divisional of U.S. application Ser. No. 11/447,668 (filed Jun. 6, 2006), which claims priority to U.S. provisional Application No. 60/688,013 (filed Jun. 6, 2005), each of which is incorporated herein by reference.

GOVERNMENT RIGHTS STATEMENT

This invention was made with Government support under Grant No. 1 R41 RR019159-01 awarded by the National Institutes of Health. The Government has certain rights to the invention.

FIELD OF THE INVENTION

The present invention generally relates to robotic surgical systems and in particular, to a laparoscopic ultrasound robotic surgical system useful for performing minimally invasive surgical procedures.

BACKGROUND OF THE INVENTION

Minimally invasive surgery offers many benefits over traditional open surgery techniques, including less pain, shorter hospital stays, quicker return to normal activities, minimal scarring, reduced recovery time, and less injury to tissue. Consequently, demand for minimally invasive surgery using robotic surgical systems is strong and growing.

Laparoscopy is a type of minimally invasive surgery in which a small incision is made in the abdominal wall through which an instrument called a laparoscope is inserted to permit anatomic structures within the abdomen and pelvis to be seen. The abdominal cavity is commonly distended and made visible by the instillation of absorbable gas such as carbon dioxide. Tubes may be pushed through the same or different incisions in the skin so that probes or other instruments can be introduced to a surgical site. In this way, a number of surgical procedures can be performed without the need for a large or open cavity surgical incision.

One disadvantage of laparoscopy, however, is the inability to manually palpate hidden or solid organs. Laparoscopic Ultrasound ("LUS") allows the surgeon to overcome this limitation by providing visualization of deeper structures. In fact, even when open cavity operations are performed, intraoperative ultrasonography may be significantly more sensitive at detecting otherwise occult lesions within anatomic structures than bimanual palpation.

As an example, intraoperative ultrasonography of the liver is useful in a variety of clinical settings during laparoscopic surgery. These include: staging and assessment of the liver, including ultrasound-guided needle biopsy, liver tumor ablation, and evaluation of the liver prior to laparoscopic liver resection.

For resection procedures, surgeons should have the ability to perform accurate staging of the liver and other sites to rule out metastatic disease prior to resection. The addition of LUS to standard laparoscopy improves the diagnosis of metastases over conventional preoperative diagnostic methods.

Ultrasound-directed liver biopsy is an important component of hepatic staging and assessment. When a lesion is identified by ultrasound, needle biopsy is necessary to confirm the findings histologically. Current practice requires manual free-hand LUS in conjunction with free-hand positioning of the biopsy needle under ultrasound guidance.

For the treatment of unresectable metastases, increasing interest has been focused on ablative approaches such as radiofrequency ("RF"), cryotherapy, microwave, or chemical ablation. While interstitial ablation can be performed percutaneously or during open surgery, laparoscopic ablation has significant advantages. First, unlike percutaneous therapy, laparoscopy can identify both hepatic and extrahepatic metastases not visualized on preoperative imaging, which misses significant tumors in about 10% to 20% of patients with colorectal liver metastases. Second, laparoscopic or operative ultrasound ("US") has been shown to be significantly more accurate than transabdominal US, CT or MR at visualizing liver lesions. Further, operative approaches, including laparoscopy, permit mobilization of structures away from a surface tumor that may be thermally injured during RF ablation. Percutaneous ablation and laparoscopic ablation both typically require general anesthesia and an overnight hospital stay. Laparoscopy, on the other hand, does not impose a significantly greater burden on the patient.

While ablation promises advantages compared to other approaches, the technical difficulty of manipulating the ultrasound probe, aligning the ultrasound probe with the ablation probe, and placement of the ablation probe demands considerable expertise. The surgeon must precisely place the ablation probe tip within the volumetric center of the tumor in order to achieve adequate destruction of the tumor and a 1 cm zone of surrounding normal parenchyma. Tumors are identified by preoperative imaging, primarily CT and MR, and then laparoscopically localized by LUS.

One major limitation of ablative approaches is the lack of accuracy in probe tip placement within the center of the tumor. This is particularly important, as histologic margins cannot be assessed after ablation as is done with hepatic resection. In addition, manual guidance often requires multiple passes and repositioning of the probe tip, further increasing the risk of bleeding and tumor dissemination. Intraoperative ultrasound provides excellent visualization of tumors and provides guidance for RF probe placement, but its 2D-nature and dependence on the sonographer's skill limit its effectiveness.

Although laparoscopic instrumentation and techniques are beginning to be extended to resection of the liver, loss of the surgeon's tactile sense makes it difficult to assess the safe margins of resection necessary for safe parenchymal transection. Lack of clear visualization and mapping of intrahepatic structures with current LUS techniques could result in catastrophic injury to major adjacent structures. The surgeon must carefully examine the liver by ultrasound prior to resection in order to rule out additional tumors which may preclude curative therapy. Surgeons also require ultrasound to determine and plan safe and complete resection with sufficient surgical margin clearance.

Despite its theoretical advantages, intraoperative LUS is not widely practiced for such uses as laparoscopic liver cancer surgery. To expand usage in this and other applications, advances in LUS robotic surgical systems that improve surgeon efficiency in performing minimally invasive surgical procedures, as well as the ease of using those systems is desirable.

For example, optimization of LUS for hepatic surgery may significantly improve the clinical management of patients. In addition to minimizing morbidity and discomfort, an improved LUS robotic surgical system may significantly reduce costs. Faster, more accurate, and more complete assessment of the liver may be performed by experts, as well as potentially by surgeons who are not experts in intraoperative ultrasonography of the liver.

Image-guided biopsy of sometimes small and inaccessible liver lesions may be facilitated. Advanced LUS robotic tools could increase the use of resection as a definitive treatment for larger and less favorably placed tumors. Improved real-time guidance for planning, delivery and monitoring of ablative therapy may also provide the missing tool needed to allow accurate and effective application of this promising therapy.

OBJECTS AND SUMMARY OF THE INVENTION

Accordingly, one object of various aspects of the present invention is a laparoscopic ultrasound robotic surgical system and robotic assisted laparoscopic ultrasound methods that are easy to use and promote surgeon efficiency.

Another object of various aspects of the present invention is a laparoscopic ultrasound robotic surgical system and robotic assisted laparoscopic ultrasound methods that provide faster, more accurate and complete assessment of anatomic structures.

Another object of various aspects of the present invention is a laparoscopic ultrasound robotic surgical system and robotic assisted laparoscopic ultrasound methods that provide robotically generated intra-operative 3D ultrasound images of an anatomic structure using surgeon trained trajectories.

Another object of various aspects of the present invention is a laparoscopic ultrasound robotic surgical system and robotic assisted laparoscopic ultrasound methods that provide flexible display of ultrasound images on a display screen.

Still another object of various aspects of the present invention is a laparoscopic ultrasound robotic surgical system and robotic assisted laparoscopic ultrasound methods that provide assistance in guiding a tool to a target on an anatomic structure.

These and additional objects are accomplished by the various aspects of the present invention, wherein briefly stated, one aspect is laparoscopic ultrasound robotic surgical system comprising: a first robotic arm mechanically coupled to an ultrasound probe; a second robotic arm mechanically coupled to a surgery related device; a master manipulator; a control switch having user selectable first and second modes; and a processor configured to cause the second robotic arm to be locked in position and the first robotic arm to move the ultrasound probe according to user manipulation of the master manipulator when the control switch is in the first mode, and cause the second robotic arm to manipulate the tool according to manipulation of the master manipulator and the first robotic arm to move the ultrasound probe according to stored instructions upon detection of a user command associated with the stored instructions when the control switch is in the second mode.

Another aspect is a method for providing robotic assisted laparoscopic ultrasound, comprising: storing a current ultrasound probe position and orientation upon detection of a start of training indication; and periodically storing ultrasound probe positions and orientations to define a trajectory of positions and orientations until detection of an end of training indication.

Another aspect is a method for providing robotic assisted laparoscopic ultrasound, comprising: capturing an ultrasound image using an ultrasound probe disposed at a position and orientation; storing information of the position and orientation; generating a clickable thumbnail of the ultrasound image; associating the stored position and orientation with the clickable thumbnail; and displaying the clickable thumbnail on a display screen.

Still another aspect is a method for providing robotic assisted laparoscopic ultrasound, comprising: displaying an ultrasound view of an anatomic structure in a patient as a registered overlay to a camera view of the anatomic structure; receiving information of a target marked on the ultrasound view; determining a path for a tool to travel to the target within the patient; and generating a virtual fixture to assist in electronically constraining the tool to travel over the determined path.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
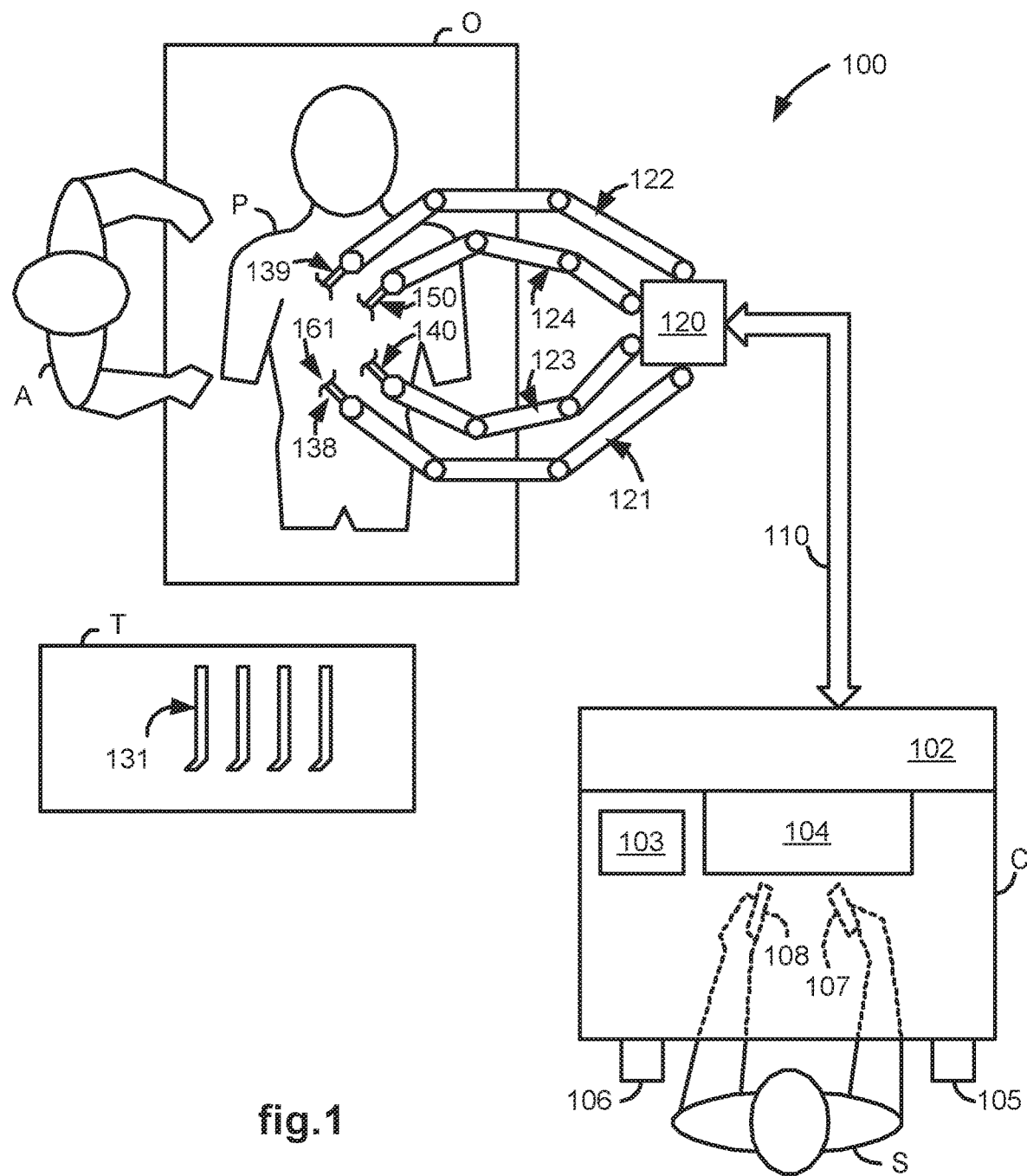
FIG. 1 illustrates a top view of an operating room employing a laparoscopic ultrasound robotic surgical system utilizing aspects of the present invention.

FIG. 1 illustrates, as an example, a top view of an operating room employing a robotic surgical system. The robotic surgical system in this case is a Laparascopic Ultrasound Robotic Surgical System 100 including a Console ("C") utilized by a Surgeon ("S") while performing a minimally invasive diagnostic or surgical procedure with assistance from one or more Assistants ("A") on a Patient ("P") who is reclining on an Operating table ("O").

The Console includes a Master Display 104 (also referred to herein as a "Display Screen") for displaying one or more images of a surgical site within the Patient as well as perhaps other information to the Surgeon. Also included are Master Input Devices 107 and 108 (also referred to herein as "Master Manipulators"), one or more Foot Pedals 105 and 106, a Microphone 103 for receiving voice commands from the Surgeon, and a Processor 102. The Master Input Devices 107 and 108 may include any one or more of a variety of input devices such as joysticks, gloves, trigger-guns, hand-operated controllers, or the like. The Processor 102 is preferably a personal computer that may be integrated into the Console or otherwise connected to it in a conventional manner.

The Surgeon performs a minimally invasive surgical procedure by manipulating the Master Input Devices 107 and 108 so that the Processor 102 causes their respectively associated Slave Arms 128 and 129 (also referred to herein as "Slave Manipulators") to manipulate their respective removably coupled and held Surgical Instruments 138 and 139 (also referred to herein as "Tools") accordingly, while the Surgeon views three-dimensional ("3D") images of the surgical site on the Master Display 104.

The Tools 138 and 139 are preferably Intuitive Surgical's proprietary EndoWrist™ articulating instruments, which are modeled after the human wrist so that when added to the motions of the robot arm holding the tool, they allow a full six degrees of freedom of motion, which is comparable to the natural motions of open surgery. Additional details on such tools may be found in commonly owned U.S. Pat. No. 5,797,900 entitled "Wrist Mechanism for Surgical Instrument for Performing Minimally Invasive Surgery with Enhanced Dexterity and Sensitivity," which is incorporated herein by this reference. At the operating end of each of the Tools 138 and 139 is a manipulatable end effector such as a clamp, grasper, scissor, stapler, blade, needle, or needle holder.

The Master Display 104 has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The Surgeon sits comfortably and looks into this display throughout surgery, making it an ideal place for the Surgeon to display and manipulate 3-D intraoperative imagery.

A Stereoscopic Endoscope 140 (also referred to as a "Laparoscope") provides right and left camera views to the Processor 102 so that it may process the information according to programmed instructions and cause it to be displayed on the Master Display 104. A Laparoscopic Ultrasound ("LUS") Probe 150 provides two-dimensional ("2D") ultrasound image slices of an anatomic structure to the Processor 102 so that the Processor 102 may generate a 3D ultrasound computer model of the anatomic structure and cause the 3D computer model (or alternatively, 2D "cuts" of it) to be displayed on the Master Display 104 as an overlay to the endoscope derived 3D images or within a Picture-in-Picture ("PIP") in either 2D or 3D and from various angles and/or perspectives according to Surgeon or stored program instructions.

Each of the Tools 138 and 139, as well as the Endoscope 140 and LUS Probe 150, is preferably inserted through a cannula or trocar (not shown) or other tool guide into the Patient so as to extend down to the surgical site through a corresponding minimally invasive incision such as Incision 166. Each of the Slave Arms 121-124 is conventionally formed of linkages which are coupled together and manipulated through motor controlled joints (also referred to as "active joints"). Setup Arms (not shown) comprising linkages and setup joints are used to position the Slave Arms 121-124 vertically and horizontally so that their respective surgical related instruments may be coupled for insertion into the cannulae.

The number of surgical tools used at one time and consequently, the number of slave arms being used in the System 100 will generally depend on the diagnostic or surgical procedure and the space constraints within the operating room, among other factors. If it is necessary to change one or more of the tools being used during a procedure, the Assistant may remove the tool no longer being used from its slave arm, and replace it with another tool, such as Tool 131, from a Tray ("T") in the Operating Room.

Preferably, the Master Display 104 is positioned near the Surgeon's hands so that it will display a projected image that is oriented so that the Surgeon feels that he or she is actually looking directly down onto the surgical site. To that end, an image of the Tools 138 and 139 preferably appear to be located substantially where the Surgeon's hands are located even though the observation points (i.e., that of the Endoscope 140 and LUS Probe 150) may not be from the point of view of the image.

In addition, the real-time image is preferably projected into a perspective image such that the Surgeon can manipulate the end effector of a Tool, 138 or 139, through its associated Master Input Device, 107 or 108, as if viewing the workspace in substantially true presence. By true presence, it is meant that the presentation of an image is a true perspective image simulating the viewpoint of an operator that is physically manipulating the Tools. Thus, the Processor 102 transforms the coordinates of the Tools to a perceived position so that the perspective image is the image that one would see if the Endoscope 140 was looking directly at the Tools from a Surgeon's eye-level during an open cavity procedure.

The Processor 102 performs various functions in the System 100. One important function that it performs is to translate and transfer the mechanical motion of Master Input Devices 107 and 108 to their associated Slave Arms 121 and 122 through control signals over Bus 110 so that the Surgeon can effectively manipulate their respective Tools 138 and 139. Another important function is to implement the various methods described herein providing a robotic assisted LUS capability.

Although described as a processor, it is to be appreciated that the Processor 102 may be implemented in practice by any combination of hardware, software and firmware. Also, its functions as described herein may be performed by one unit, or divided up among different components, each of which may be implemented in turn by any combination of hardware, software and firmware.

Prior to performing a minimally invasive surgical procedure, ultrasound images captured by the LUS Probe 150, right and left 2D camera images captured by the stereoscopic Endoscope 140, and end effector positions and orientations as determined using kinematics of the Slave Arms 121-124 and their sensed joint positions, are calibrated and registered with each other.

In order to associate the ultrasound image with the rest of the surgical environment, both need to be expressed in the same coordinate frame. Typically, the LUS Probe 150 is either labeled with markers and tracked by a tracking device such as the Optotrak® position sensing system manufactured by Northern Digital Inc. of Ontario, Canada, or held by a robot with precise joint encoders. Then the rigid transformation between the ultrasound image and the frame being tracked is determined (which is typically referred to as the ultrasound calibration).

For example, using the Optotrak® frame for the ultrasound calibration, the ultrasound image generated by the LUS Probe 150 is calibrated to an Optotrak® rigid body using an AX=XB formulation. "AX=XB" is a rubric for a class of calibration/registration problem commonly encountered in computer vision, surgical navigation, medical imaging, and robotics. The mathematical techniques are well known. See, e.g., E. Boctor, A. Viswanathan, M. Chioti, R. Taylor, G. Fichtinger, and G. Hager, "A Novel Closed Form Solution for Ultrasound Calibration," *International Symposium on Biomedical Imaging*, Arlington, Va., 2004, pp. 527-530.

"A" and "B" in this case, are transformations between poses of the Optotrak® rigid body (A) and the ultrasound image (B). Thus, "X" is the transformation from the ultrasound image to the rigid body.

To perform the ultrasound calibration, the LUS Probe 150 may be placed in three known orientations defined by the AX=XB calibration phantom. The ultrasound image frame may then be defined by three fiducials which appear in each of the three poses. The three poses allow three relative transformations based on Optotrak® readings (A) and three relative transformations based on the ultrasound images (B) for the AX=XB registration.

Camera calibration is a common procedure in computer vision applications. As an example, in order to determine the intrinsic and extrinsic parameters of the Endoscope 140, a checkerboard phantom with a multi-plane formulation provided by the Caltech Camera Calibration Toolbox may be used. To construct the phantom, Optotrak® markers are added to a typical checkerboard video calibration phantom, and each corner of the checkerboard is digitized using a calibrated Optotrak® pointer. Thus, the corner positions may be reported with respect to the Optotrak®.

The calibration may then be performed by placing the phantom in view of the Endoscope 140 in several dozen orientations, and recording both stereo image data and Optotrak® readings of the four checkerboard corners. The images may then be fed into the calibration toolbox, which determines the intrinsic and extrinsic camera parameters, as well as the 3D coordinates of the grid corners in the camera frame. These coordinates may then be used with the Optotrak® readings to perform a point-cloud to point-cloud registration between the Endoscope 140 rigid body and camera frame.

The Controller 102 is configured to use the robot kinematics to report a coordinate frame for the LUS Probe 150 tip relative to the Endoscope 140. However, due to inaccuracies in the setup joint encoders, both of these coordinate frames may be offset from their correct values. Thus, it may be necessary to register the offsets between the real camera frame of the Endoscope 140 and the camera frame calculated from the kinematics as well as between the real and kinematic LUS Probe 150 frames. With this complete, the kinematics may be used in place of the Optotrak® readings to determine ultrasound image overlay placement.

As long as the position of the Endoscope 140 doesn't overly change, a constant transformation may be assumed between the kinematic tool tip and the laparoscopic Optotrak® rigid body. Using an AX=XB formulation, the LUS Probe 150 may be moved, for example, to several positions, and the static offset between the tool tip and Optotrak® rigid body registered. Knowing this offset, the Endoscope 140 offset may be calculated directly:

$$C_{CD} = D_{LusD}(C_{LusUrb})^{-1}T_{OUrb}(T_{OErb})^{-1}F_{CErb} \quad (1)$$

where $C_{CD}$ is the camera offset from the real Endoscope 140 (also referred to herein simply as the "camera") frame to the camera frame calculated from the kinematics, $F_{CErb}$ is the transformation from the camera to the endoscope rigid body, $T_{OUrb} \cdot (T_{OErb})^{-1}$ is the transformation from the camera rigid body to the LUS rigid body, $C_{LusUrb}$ is the transformation from the LUS rigid body to the kinematic ultrasound tool tip, and $D_{LusD}$ is the reading from the Controller 102 giving the transformation from the kinematic ultrasound tool tip to a fixed reference point associated with the Slave Arms 121-124.

However, the aforedescribed registration should be redone each time the camera is moved, thus making it best suited for pre-operative calibration and registration. For intra-operative, the registration may be better performed using video tracking of a visual marker on the LUS Probe 150 instead of the Optotrak® readings. Thus, if the camera were moved while using tool tracking, the registration can be corrected on the fly as the tool is tracked. For additional details on tool tracking, see, e.g., commonly owned U.S. patent application Ser. No. 11/130,471 entitled "Methods and system for performing 3-D tool tracking by fusion of sensor and/or camera derived data during minimally invasive surgery," filed May 16, 2005, which is incorporated herein by reference. In addition to, or alternatively, manual registration of ultrasound and camera images may be performed using conventional grab, move and rotate actions on a 3D ultrasound computer model of an anatomic structure, so that the computer model is properly registered over a camera model of the anatomic structure in the Master Display 104.

Slave Arms 123 and 124 may manipulate the Endoscope 140 and LUS Probe 150 in similar manners as Slave Arms 121 and 122 manipulate Tools 138 and 139. When there are only two master input devices in the system, however, such as Master Input Devices 107 and 108 in the System 100, in order for the Surgeon to manually control movement of either the Endoscope 140 or LUS Probe 150, it may be required to temporarily associate one of the Master Input Devices 107 and 108 with the Endoscope 140 or the LUS Probe 150 that the Surgeon desires manual control over, while its previously associated Tool and Slave Manipulator are locked in position.

Figure 2:
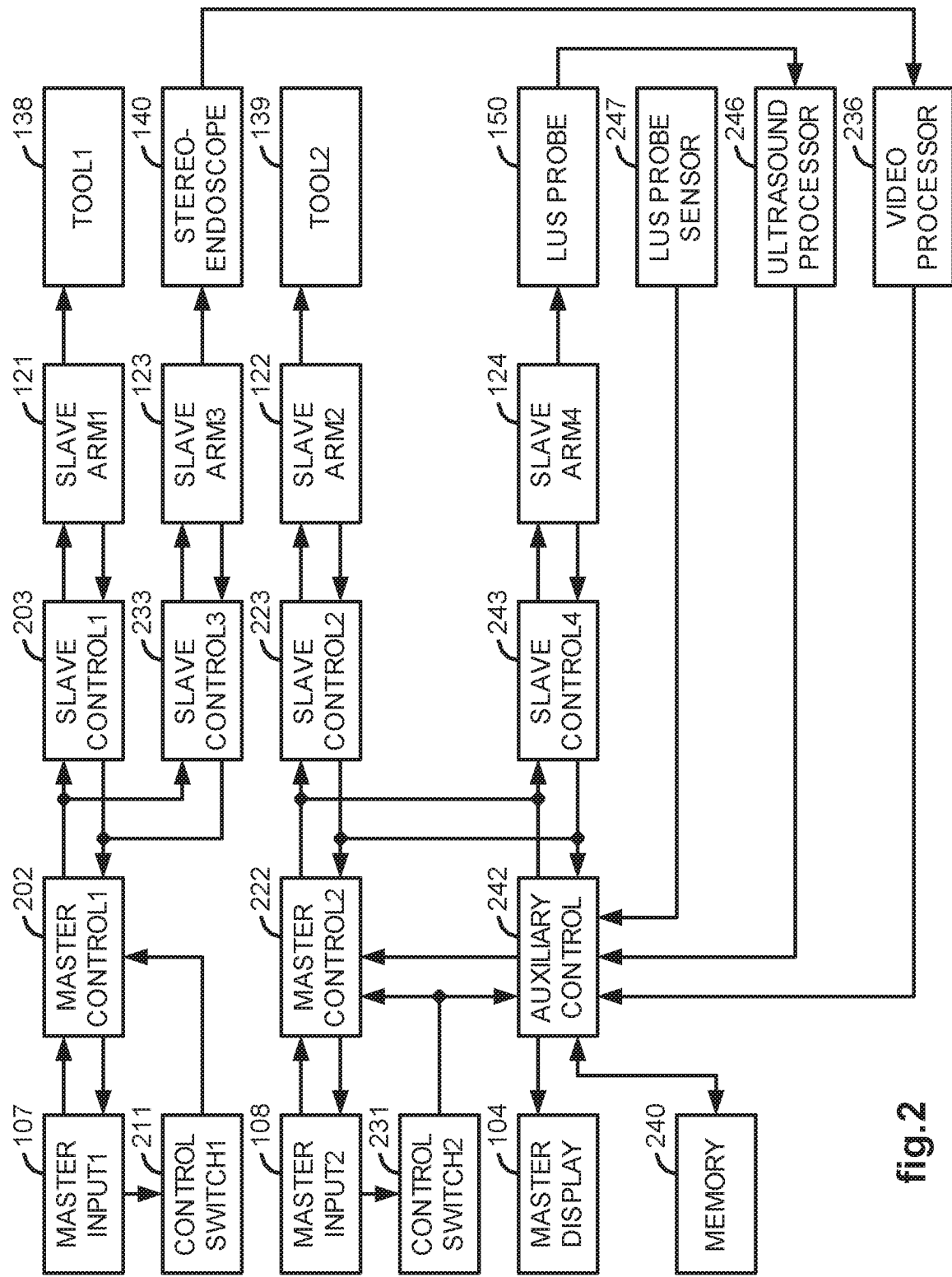
FIG. 2 illustrates a block diagram of a laparoscopic ultrasound robotic surgical system utilizing aspects of the present invention.

FIG. 2 illustrates, as an example, a block diagram of the LUS Robotic Surgical System 100. In this system, there are two Master Input Devices 107 and 108. Master Input Device 107 controls movement of either a Tool 138 or a stereoscopic Endoscope 140, depending upon which mode its Control Switch Mechanism 211 is in, and Master Input Device 108 controls movement of either a Tool 139 or a LUS Probe 150, depending upon which mode its Control Switch Mechanism 231 is in.

The Control Switch Mechanisms 211 and 231 may be placed in either a first or second mode by a Surgeon using voice commands, switches physically placed on or near the Master Input Devices 107 and 108, Foot Pedals 105 and 106 on the Console, or Surgeon selection of appropriate icons or other graphical user interface selection means displayed on the Master Display 104 or an auxiliary display (not shown).

When Control Switch Mechanism 211 is placed in the first mode, it causes Master Controller 202 to communicate with Slave Controller 203 so that manipulation of the Master Input 107 by the Surgeon results in corresponding movement of Tool 138 by Slave Arm 121, while the Endoscope 140 is locked in position. On the other hand, when Control Switch Mechanism 211 is placed in the second mode, it causes Master Controller 202 to communicate with Slave Controller 233 so that manipulation of the Master Input 107 by the Surgeon results in corresponding movement of Endoscope 140 by Slave Arm 123, while the Tool 138 is locked in position.

Similarly, when Control Switch Mechanism 231 is placed in the first mode, it causes Master Controller 222 to communicate with Slave Controller 223 so that manipulation of the Master Input 108 by the Surgeon results in corresponding movement of Tool 139 by Slave Arm 122. In this case, however, the LUS Probe 150 is not necessarily locked in position. Its movement may be guided by an Auxiliary Controller 242 according to stored instructions in Memory 240. The Auxiliary Controller 242 also provides haptic feedback to the Surgeon through Master Input 108 that reflects readings of a LUS Probe Force Sensor 247. On the other hand, when Control Switch Mechanism 231 is placed in the second mode, it causes Master Controller 222 to communicate with Slave Controller 243 so that manipulation of the Master Input 222 by the Surgeon results in corresponding movement of LUS Probe 150 by Slave Arm 124, while the Tool 139 is locked in position.

Before switching back to the first or normal mode, the Master Input Device 107 or 108 is preferably repositioned to where it was before the switch to the second mode of Control Switch 211 or 231, as the case may be, or kinematic relationships between the Master Input Device 107 or 108 and its respective Tool Slave Arm 121 or 122 is readjusted so that upon switching back to the first or normal mode, abrupt movement of the Tool 138 or 139 does not occur. For additional details on control switching, see, e.g., commonly owned U.S. Pat. No. 6,659,939 "Cooperative Minimally Invasive Telesurgical System," which is incorporated herein by this reference.

The Auxiliary Controller 242 also performs other functions related to the LUS Probe 150 and the Endoscope 140. It receives output from a LUS Probe Force Sensor 247, which senses forces being exerted against the LUS Probe 150, and feeds the force information back to the Master Input Device 108 through the Master Controller 222 so that the Surgeon may feel those forces even if he or she is not directly controlling movement of the LUS Probe 150 at the time. Thus, potential injury to the Patient is minimized since the Surgeon has the capability to immediately stop any movement of the LUS Probe 150 as well as the capability to take over manual control of its movement.

Another key function of the Auxiliary Control 242 is to cause processed information from the Endoscope 140 and the LUS Probe 150 to be displayed on the Master Display 104 according to user selected display options. As will be described in more detail below, such processing includes generating a 3D ultrasound image from 2D ultrasound image slices received from the LUS Probe 150 through an Ultrasound Processor 246, causing either 3D or 2D ultrasound images corresponding to a selected position and orientation to be displayed in a picture-in-picture window of the Master Display 104, and causing either 3D or 2D ultrasound images of an anatomic structure to overlay a camera captured image of the anatomic structure being displayed on the Master Display 104.

Although shown as separate entities, the Master Controllers 202 and 222, Slave Controllers 203, 233, 223, and 243, and Auxiliary Controller 242 are preferably implemented as software modules executed by the Processor 102, as well as certain mode switching aspects of the Control Switch Mechanisms 211 and 231. The Ultrasound Processor 246 and Video Processor 236, on the other hand, are separate boards or cards typically provided by the manufacturers of the LUS Probe 150 and Endoscope 140 that are inserted into appropriate slots coupled to or otherwise integrated with the Processor 102 to convert signals received from these image capturing devices into signals suitable for display on the Master Display 104 and/or for additional processing by the Auxiliary Controller 242 before being displayed on the Master Display 104.

Figure 3:
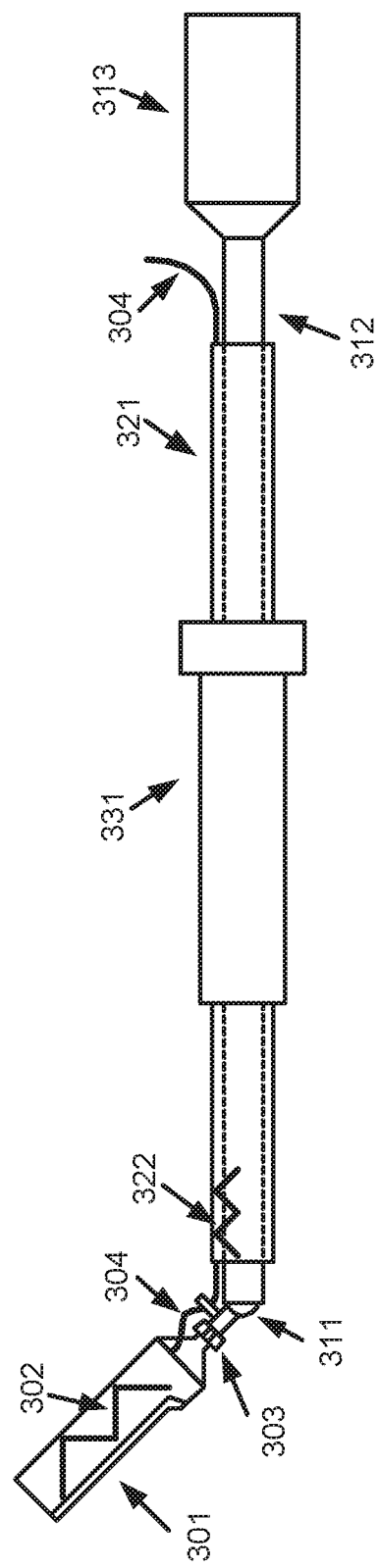
FIG. 3 illustrates a laparoscopic ultrasound probe utilizing aspects of the present invention.

FIG. 3 illustrates a side view of one embodiment of the LUS Probe 150. The LUS Probe 150 is a dexterous tool with preferably two distal degrees of freedom, permitting reorientation of LUS Sensor 301 through, for example, approximately ±80° in distal "pitch" and "yaw", and ±240° in "roll" about a ball joint type, pitch-yaw mechanism 311 (functioning as and also referred to herein as a "Wrist" mechanism). Opposing pairs of Drive Rods or Cables (not shown) physically connected to a proximal end of the LUS Sensor 301 and extending through an internal passage of Elongated Shaft 312 mechanically control pitch and yaw movement of the LUS Sensor 301 using conventional push-pull type action. This flexibility of the LUS Probe 150 (provided by the pitch/yaw wrist mechanism) is especially useful in optimally orienting the LUS Probe 150 for performing ultrasonography on an anatomic structure during a minimally invasive surgical procedure.

The LUS Sensor 301 captures 2D ultrasound slices of a proximate anatomic structure, and transmits the information back to the Processor 102 through LUS Cable 304. Although shown as running outside of the Elongated Shaft 312, the LUS Cable 304 may also extend within it. A Clamshell Sheath 321 encloses the Elongate Shaft 312 and LUS Cable 304 to provide a good seal passing through a Cannula 331 (or trocar). Fiducial Marks 302 and 322 are placed on the LUS Sensor 301 and the Sheath 321 for video tracking purposes.

A force sensing capability is provided by Strain Gauges 303 which provide direct feedback of how hard the LUS Probe 150 is pushing on a structure being sonographed, supplementing whatever limited feedback is available from joint motor torques. Potential uses of this information include: providing a redundant safety threshold check warning the Surgeon or preventing motion into the structure if forces get too great; providing the Surgeon with an approved haptic appreciation of how hard he or she is pushing on a structure; and possibly permitting some measure of compensation for unmodeled deflections of the Pitch-Yaw or "Wrist" Mechanism 311 which are not detected for some reason by joint position sensors or encoders. The Strain Gauges 303 in this case serve the function of the LUS Probe Force Sensor 247 as previously described in reference to FIG. 2.

Robotic assisted LUS has the potential to reduce variability in the ultrasound images produced, compared to freehand scanning, and can reduce operator workload and difficulty. Behaviors as simple as rocking the LUS Probe 150 back and forth can maintain an updated 3D ultrasound image without operator intervention. More complicated behaviors can include movement of the LUS Probe 150 along the surface of a target anatomical structure in a methodical pattern to generate a full image of the target, or reliably returning to a previously scanned probe location and orientation.

Figure 4:
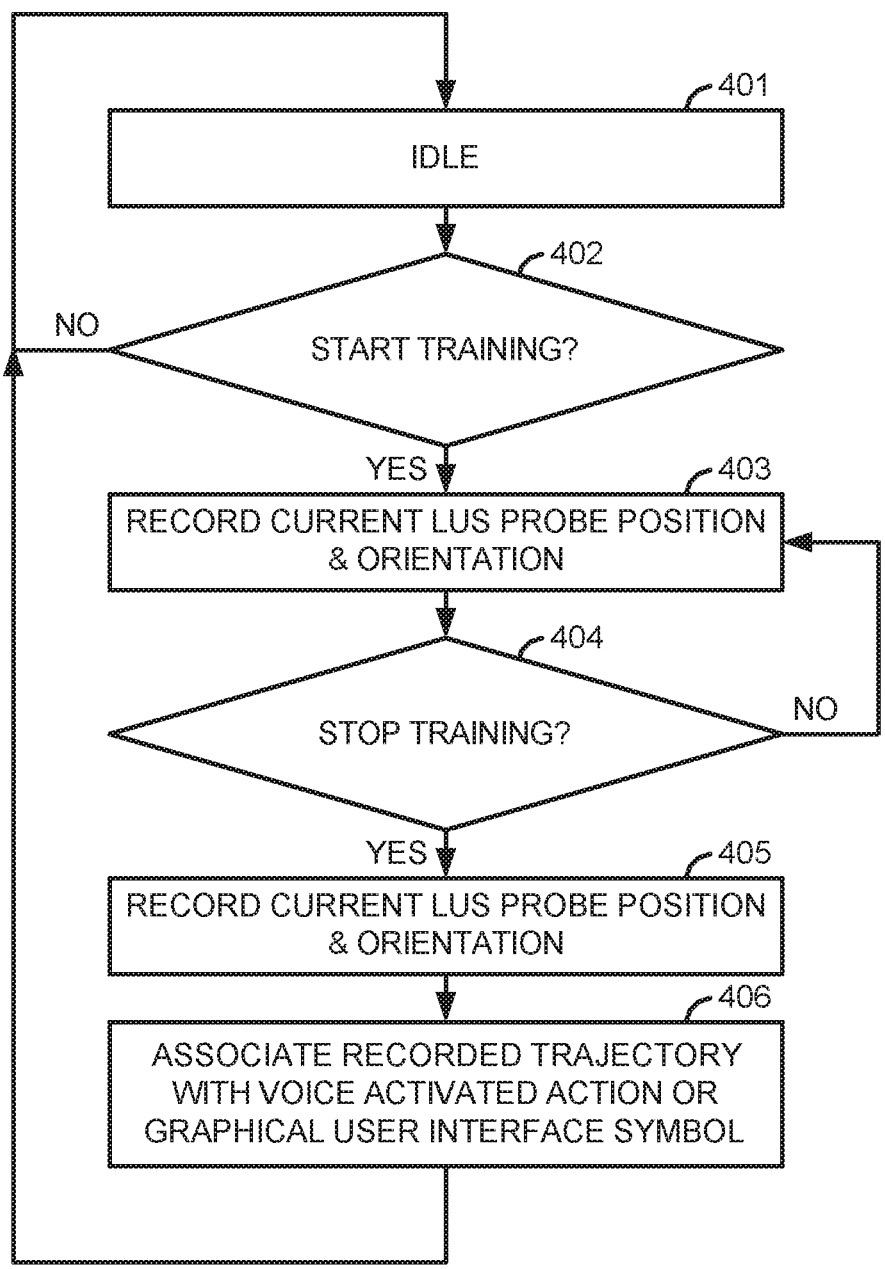
FIG. 4 illustrates a flow diagram of a method for training a LUS robotic surgical system to robotically move a LUS probe in a trained manner upon command, utilizing aspects of the present invention.

FIG. 4 illustrates, as an example, a flow diagram of a method for training the Auxiliary Controller 242 (i.e., providing it with stored instructions) to cause the LUS Probe 150 to be robotically moved in the trained manner upon command, in order to capture a sequence of 2D ultrasound image slices of an anatomic structure, which are used by the Auxiliary Controller 242 to generate a 3D computer model of the structure. Prior to performing the training, the Control Switch Mechanism 231 is placed in its second mode so that the Surgeon may move the LUS Probe 150 for training purposes by manipulating the Master Input Device 108. After performing training, the Control Switch Mechanism 231 is then placed back into its first or normal mode so that the Surgeon may manipulate the Tool 139 to perform a minimally invasive surgical procedure using the Master Input Device 108.

In 401, the training module is initially idle (i.e., it is not being executed by the Processor 102). In 402, the Processor 102 (or a training module agent running in the background) may periodically check whether a start of training indication is received. Alternatively, the start of training indication may act as an interrupt which initiates running of the training module. The start of training indication may be initiated by a Surgeon through a recognized voice command, selection of a training option on a graphical user interface displayed on the Master Display 104, a switch mechanism that may physically be located on the corresponding Master Control Input 108 or other convenient location accessible to the Surgeon, or any other conventional means.

After the start of training indication is detected, in 403, the training module records or stores the current LUS Probe 150 position and orientation, and periodically (or upon Surgeon command) continues to do so by looping around 403 and 404 until a stop training indication is detected or received. The stop training indication in this case may also be initiated by the Surgeon in the same manner as the start of training indication, or it may be initiated in a different, but other conventional manner. After the stop training indication is detected or received, a last position and orientation of the LUS Probe 150 is recorded or stored.

Between the start and stop of training, the Surgeon moves the LUS Probe 150 and the Processor 102 stores its trajectory of points and orientations so that they may be retraced later upon command. In one type of training, the Surgeon moves the LUS Probe 150 back and forth near an anatomic structure in order to capture a sequence of 2D ultrasound image slices from which a 3D version (or computer model) of the anatomic structure may be rendered by the Processor 102. In another type of training, the Surgeon move the LUS Probe 150 once or more times along the surface of the anatomic structure in order to capture a different sequence of 2D ultrasound image slices from which a 3D version (or computer model) of the anatomic structure may be rendered by the Processor 102.

Although described as recording the positions and orientations of the LUS Probe 150, in practice, the active joint positions of its Slave Arm 124 are stored instead since their measurements are directly obtainable through encoders attached to each of the joints and their positions correspond to the LUS Probe 150 positions and orientations.

After storing the trajectory of positions and orientations of the LUS Probe 150 in the Memory 240, the trajectory is then associated with a means for the Surgeon to command the Auxiliary Controller 242 to move the LUS Probe 150 in the desired fashion. For example, the trajectory may be associated with a voice command which upon its detection, the Auxiliary Controller 242 causes the Slave Arm 124 to move the LUS Probe 150 back and forth along the stored trajectory of positions and orientations. Likewise, the trajectory may also be associated with a user selectable option on a graphical user interface displayed on the Master Display 104, or it may be associated with a switch mechanism such as a button or unused control element on the Master Input Device 108. It may also be associated with the depression of the Foot Pedal 106, so that the Auxiliary Controller 242 causes the Slave Arm 124 to move the LUS Probe 150 back and forth along the stored trajectory of positions and orientations as long as the Foot Pedal 106 is being depressed, and stops such motion once the Surgeon takes his or her foot off the Foot Pedal 106.

Figure 5:
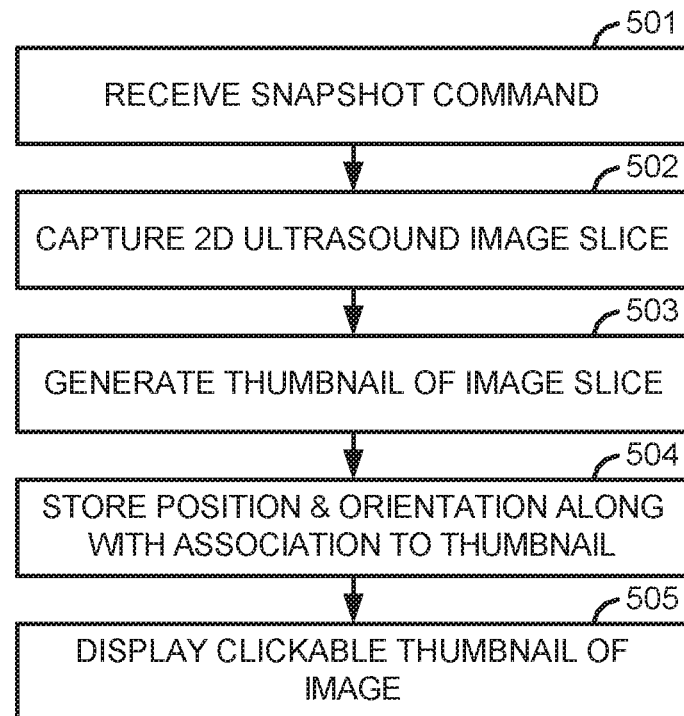
FIG. 5 illustrates a flow diagram of a method for generating a clickable thumbnail image that allows a user to command that a LUS probe be automatically moved to a position and orientation from which the image was captured, utilizing aspects of the present invention.

FIG. 5 illustrates, as an example, a flow diagram of a method for generating clickable thumbnail images corresponding to LUS Probe 150 positions and orientations that are stored in Memory 240, so that when the Surgeon clicks on one of the thumbnail images, the Auxiliary Controller 242 causes the Slave Arm 124 to move the LUS Probe 150 to its stored position and orientation. This allows the Surgeon to move the LUS Probe 150 to see different views of an anatomic structure while the Control Switch Mechanism 231 is in its first or normal mode. Thus, the Surgeon can continue to perform a minimally invasive surgical procedure by manipulating Tool 139 using the Master Input Device 108. The method may then be combined with that described in reference to FIG. 4 in order to generate a sequence of 2D ultrasound image slices starting from that position and orientation, from which the Auxiliary Controller 242 may generate a 3D computer model rendition of the anatomic structure.

Prior to performing the method, however, the Control Switch Mechanism 231 is placed in its second mode so that the Surgeon may move the LUS Probe 150 into the desired positions and orientations by manipulating the Master Input Device 108. After generating the clickable thumbnail images, the Control Switch Mechanism 231 is then placed back into its first or normal mode so that the Surgeon may manipulate the Tool 139 to perform the minimally invasive surgical procedure using the Master Input Device 108.

In 501, the Auxiliary Controller 242 receives a snapshot command from the Surgeon. The snapshot command may be, for example, a voice command, graphical user interface selection, or switch position. In 502, the Auxiliary Controller 242 causes the LUS Probe 150 to capture a 2D ultrasound image slice, and in 503, a thumbnail of the image is generated. The thumbnail in this case may include a simple JPEG or GIF file of the captured image. In 504, the current position and orientation of the LUS Probe 150 is stored in Memory 240 along with information of its association with the thumbnail. In 505, a clickable version of the thumbnail is displayed on the Master Display 104, so that the Surgeon may command the Auxiliary Controller 242 to cause the LUS Probe to be positioned and oriented at the stored position and orientation at any time upon clicking with his or her mouse or other pointing device on the clickable thumbnail. The Surgeon may then move the LUS Probe 150 to other positions and/or orientations, and repeat 501-505 to generate additional thumbnail images.

Figure 6:
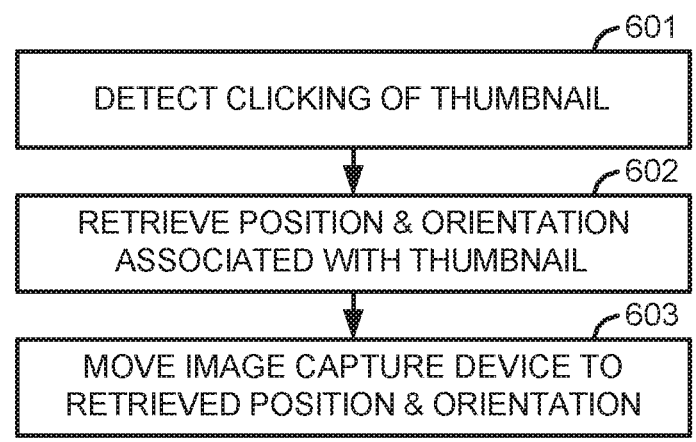
FIG. 6 illustrates a flow diagram of a method for automatically moving s LUS probe to a position and orientation associated with a clickable thumbnail image, utilizing aspects of the present invention.

FIG. 6 illustrates, as an example, a flow diagram of a method for automatically moving the LUS Probe 150 to a position and orientation associated with a clickable thumbnail upon command to do so by a Surgeon while performing a minimally invasive surgical procedure using Tool 139. In 601, the clicking of a thumbnail generated by the method described in reference to FIG. 5 is detected by, for example, a conventional interrupt handling process. Upon such detection, in 602, the Auxiliary Controller 242 is instructed by, for example, stored instructions corresponding to the interrupt handling process, to retrieve the position and orientation stored in Memory 240 which is associated with the thumbnail. The Auxiliary Controller 242 then causes the LUS Probe 150 to move to that position and orientation by appropriately controlling Slave Arm 124. Thus, the Surgeon is able to move the LUS Probe 150 to a desired position without having to change modes of the Control Switch Mechanism 231 and halt operation of the Tool 139 until the LUS Probe 150 is moved.

Figure 7:
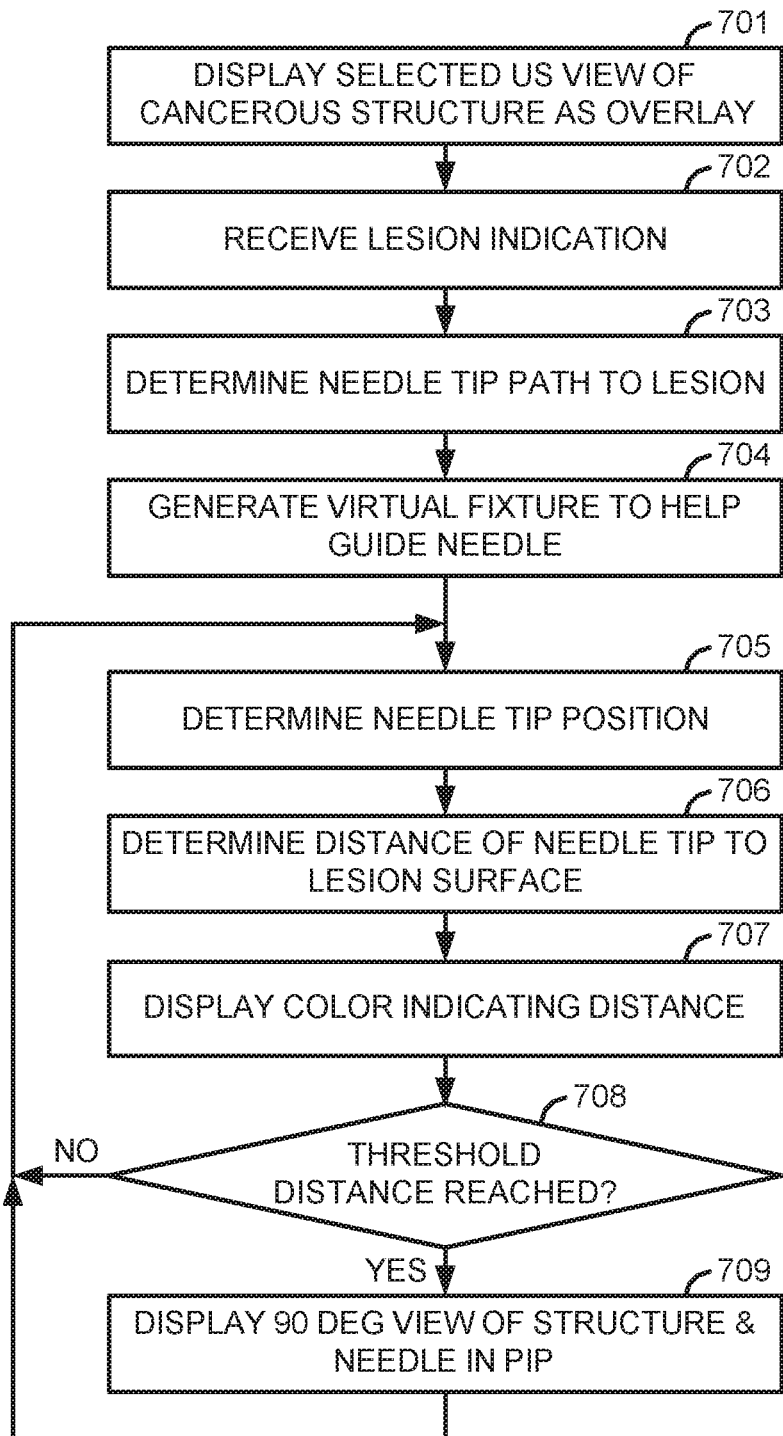
FIG. 7 illustrates a flow diagram of a method for robotically assisted needle guidance to a marked lesion of a cancerous structure, utilizing aspects of the present invention.

FIG. 7 illustrates, as an example, a flow diagram of a method for robotically assisted needle guidance and penetration into a marked lesion of a cancerous structure, which allows appreciation for the aspects of robotic assisted LUS described herein. In 701, a selected 2D ultrasound image slice view of a cancerous structure such as a liver is displayed at the proper depth on the Master Display 104 as an overlay to a 3D camera view of the cancerous structure. The selected 2D ultrasound image slice view may be a frontal view or an inner slice view as taken from a previously generated 3D ultrasound computer model of the cancerous structure.

Figure 8:
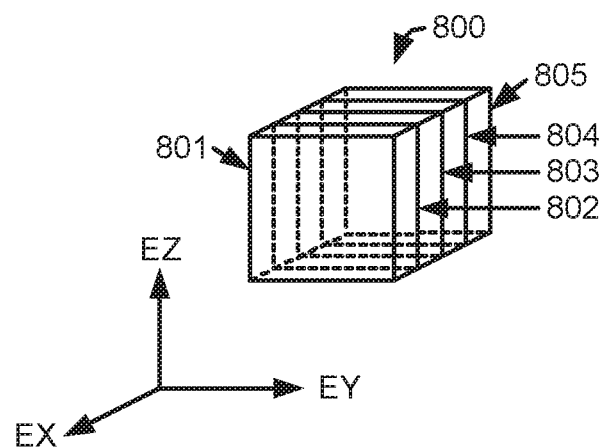
FIG. 8 illustrates a perspective view of a 3D ultrasound image of an anatomic structure in a camera reference frame with selectable 2D image slices as used in a medical robotic system utilizing aspects of the present invention.
Figure 9:
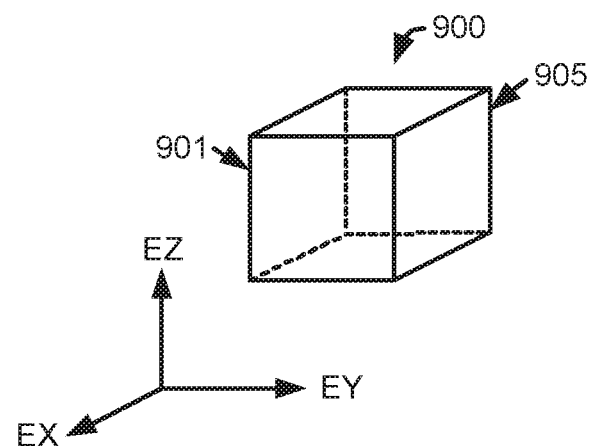
FIG. 9 illustrates a perspective view of a 3D camera view of an anatomic structure in a camera reference as used in a medical robotic system utilizing aspects of the present invention.
Figure 10:
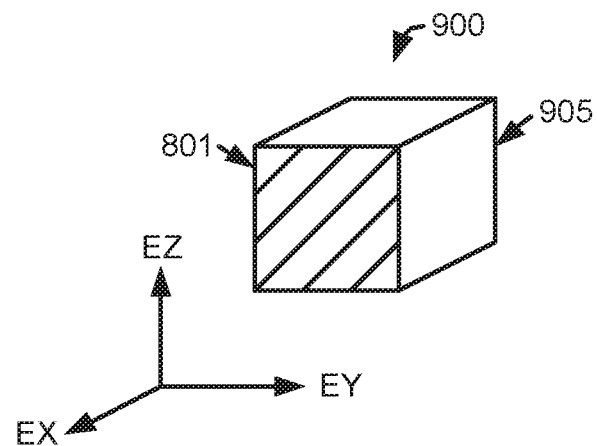
FIG. 10 illustrates a perspective view of a frontal 2D slice of a 3D ultrasound view of an anatomic structure that overlays a 3D camera view of the anatomic structure, as displayable in a medical robotic system utilizing aspects of the present invention.
Figure 11:
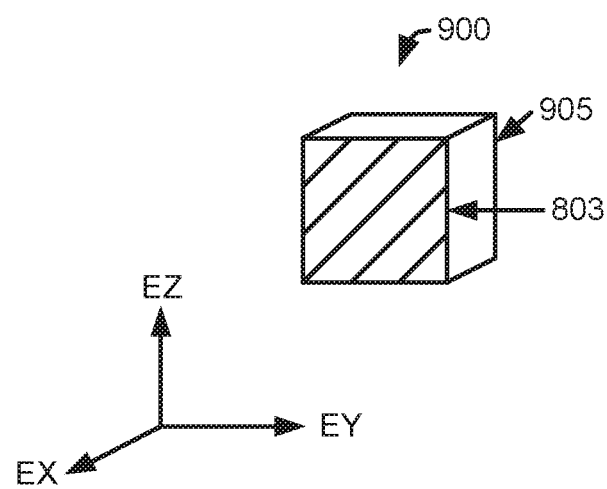
FIG. 11 illustrates a perspective view of an inner 2D slice of a 3D ultrasound view of an anatomic structure that overlays a 3D camera view of the anatomic structure, as displayable in a medical robotic system utilizing aspects of the present invention.

As an example clarifying the 701 process, FIG. 8 illustrates a simplified perspective view of a 3D ultrasound computer model 800 of the cancerous structure, which has been generated, for example, using the method described in reference to FIG. 4, and has been translated into the camera reference frame (EX, EY, EZ). FIG. 9, on the other hand, illustrates a simplified perspective view of a 3D camera view 900 of the cancerous structure as taken by the stereoscopic Endoscope 140. If the Surgeon selects a frontal slice 801 of the 3D ultrasound computer model 800 to be viewed as an overlay to the 3D camera view 900, then the overlay will appear as shown in FIG. 10. On the other hand, if the Surgeon selects one of the inner slices 802-804 of the 3D ultrasound computer model 800, such as inner slice 803, to be viewed as an overlay to the 3D camera view 900, then the overlay will appear as shown in FIG. 11 with the 2D ultrasound image slice 803 displayed at the proper depth. To avoid confusion, the portion of the 3D camera view above that depth is made transparent.

Alternatively, in 701, the surgeon may manually control movement of the LUS Probe 150 so that 2D ultrasound image slices captured by it appear as emanating in proper perspective and direction from the 3D camera image of the LUS Probe 150 in the Master Display 104. Preferably, the emanated 2D image slices being displayed in the Master Display 104 do not occlude the anatomic structure being probed. This manual approach may be particularly useful to the Surgeon for quickly spotting lesions in the anatomic structure.

In 702, the Surgeon marks lesions on the cancerous structure displayed as a result of 701. Each marked lesion is preferably marked using a designated color in order to clearly show that the Surgeon has already identified it, thereby avoiding double counting. The location in the camera reference frame (EX, EY, EZ) of each marked lesion is stored in Memory 240, and in 703, the Processor 102 determines an optimal needle tip path to that location.

In 703, the Processor 102 generates a virtual fixture to help guide the needle to the marked lesion. To generate the virtual fixture, local kinematic constraints on the Slave Arm manipulating the needle Tool may be specified by providing a table of constraints of the form:

$$(\vec{x}-\vec{x}_0) T_{A_K} (\vec{x}-\vec{x}_0) + \vec{b}_K (\vec{x}-\vec{x}_0) \leq c \qquad (2)$$

where $\vec{x}$ represents, in simplified terms, the current 6 DOF kinematic pose of a master arm, or, in more general terms, a parameterization of a Cartesian pose F linearized about some nominal pose $F_0$ so that $(\vec{x}-\vec{x}_0) \sim F_0^{-1} F$. The tables are to be updated periodically based on visual feedback, user interaction, etc.

As can be appreciated, equation (2) can be easily checked and enforced.

Similarly, a simple table-driven interface for surgeon interaction forces can be implemented approximately as follows:

$$\vec{f} \leftarrow 0; y \leftarrow \vec{x} - \vec{x}_0; \qquad (3)$$
$$\text{for } k \leftarrow 1 \text{ to N do}$$
$$\{ \varepsilon \leftarrow \vec{y}^T C_K \vec{y} + \vec{d}_K \vec{y} - e_K;$$
$$\quad \text{if } \varepsilon > 0 \text{ then } \{\vec{g} \leftarrow 2 C_K \vec{y} \; \vec{d}_K; \vec{f} \leftarrow \vec{f} + f(\varepsilon) \vec{g}/\|\vec{g}\|;$$
$$\quad \};$$
$$\};$$
output $\vec{f}$ (after limiting & spacing )

where ε corresponds, roughly, to a distance from a surface in state space and the function $f(\varepsilon)$ corresponds to a (non-linear) stiffness.

The above formulation suffices to support a variety of virtual chamfers, virtual springs, detents, etc. It is also easily extended to virtual dampers by adding velocity terms.

Now, more particularly, in the present case where it is desired to help aim an injection needle at a target in a live ultrasound image, let:

$$\vec{P}_{TROCAR} = \text{position where needle enters patient} \qquad (4)$$
$$= \text{``RCM'' point for needle insertion arm}$$

$$R_{NEEDLE} = R_0 R(\vec{\alpha}) = \text{orientation of needle arm} \qquad (5)$$

$$\vec{\alpha} = \text{vector representation for small rotation} \qquad (6)$$

$$F_{LUS} = [R_{LUS}, \vec{P}_{LUS}] = \text{pose of LUS sensor} \qquad (7)$$

$$V_{TARGET} = \text{position of target wrt LUS sensor} \qquad (8)$$

Then the basic constraint is that the needle axis (which is assumed for this example to be the $\vec{Z}$ axis of the needle driver) should be aimed at the target lesion, which will be given by $F_{LUS} \vec{V}_{TARGET}$. One metric for the aiming direction error will be:

$$\varepsilon_{AIMING}(\vec{\alpha}) = \|(R_{NEEDLE} \vec{z}) \times (F_{LUS} \vec{v}_{TARGET} - \vec{P}_{TROCAR})\|^2 \qquad (9)$$

-continued $$= \|(R(\vec{\alpha})\vec{z}) \times R_0^{-1}(F_{LUS}\vec{v}_{TARGET} - \vec{P}_{TROCAR})\|^2$$

which can be approximated as a quadratic form in $\vec{\alpha}$ and converted to a virtual fixture using the method described above. Similarly, if the position of the needle tip is $\vec{P}_{TIP}$, the penetration depth beyond the LUS target will be given by:

$$\varepsilon_{BEYOND} = (R_0 R(\vec{\alpha})\vec{z}) \cdot (F_{LUS}\vec{v}_{TARGET} - \vec{P}_{TIP}) \quad (10)$$

which can easily be transcribed into a virtual detent or barrier preventing over-penetration. Alternatively, a simple spherical attractor virtual fixture can be developed to minimize $\|F_{LUS}\vec{v}_{TARGET} - \vec{P}_{TIP}\|$.

In 705, the Processor 102 determines the needle tip position as it moves towards the target lesion, and in 706, the Processor 102 determines the distance between the needle tip position and the target lesion. The needle tip position may be determined from the Slave Arm kinematics and/or through visual tracking in the camera image.

In 707, the color of the lesion or some other object in the display changes as the needle tip gets closer to the target. For example, the color may start off as blue when the needle tip is still far away from the target, and it may change through color spectrum so that it becomes red as it nears the target. Alternatively, a bar graph or other visual indicator may be used to give a quick sense of the distance.

In 708, a determination is made whether the distance has reached a threshold distance (usually specified as some distance close to or even at the surface of the target lesion). If the threshold has not been reached, then the method loops back to 705 and continually repeats 705-708 until the threshold is reached. Once the threshold is reached, in 709, a 90 degree view of the cancerous structure and the approaching needle is shown in a picture-in-picture window of the Master Display 104. The method may then go back to 705 and repeat 705-708 as the needle penetrates the cancerous structure or withdraws back to its start position.

Although the various aspects of the present invention have been described with respect to a preferred embodiment, it will be understood that the invention is entitled to full protection within the full scope of the appended claims.

What is claimed is:

1. A medical system comprising:
   a first robotic arm mechanically coupled to an ultrasound probe that is disposed at a current location;
   a display displaying a first clickable thumbnail and a second clickable thumbnail, the first clickable thumbnail appearing on the display as a first ultrasound image slice of an object previously captured by the ultrasound probe while at a first location, the second clickable thumbnail appearing on the display as a second ultrasound image slice of the object previously captured by the ultrasound probe while at a second location; and
   a processor programmed to:
      conditioned upon a user clicking on the first clickable thumbnail:
         automatically command the first robotic arm to move the ultrasound probe from the current location to the first location; and
         after commanding the first robotic arm to automatically move the ultrasound probe from the current position to the first location and conditioned upon receiving a command associated with a first trajectory of positions, command the first robotic arm to automatically move the ultrasound probe along the first trajectory of positions; and
      conditioned upon the user clicking on the second clickable thumbnail: command the first robotic arm to automatically move the ultrasound probe from the current location to the second location.

2. The medical system according to claim 1, wherein the first trajectory of positions comprises a plurality of positions that follow a contour of the object.

3. The medical system according to claim 1, wherein the command associated with the first trajectory is a voice command.

4. The medical system according to claim 1, wherein the command associated with the first trajectory derives from a selection indicated by an option provided in a graphical user interface.

5. The medical system according to claim 1, wherein the command associated with the first trajectory derives from a selection indicated by a switch position.

6. The medical system according to claim 1, wherein the first robotic arm has a joint, and wherein the first location is identified by using information of a position of the joint when the ultrasound probe was previously at the first location.

7. The medical system according to claim 1,
   wherein the ultrasound probe was at a prior orientation when the ultrasound probe was previously at the first location, and
   wherein the processor is programmed to:
      conditioned upon the user clicking on the first clickable thumbnail, command the first robotic arm to automatically orient the ultrasound probe to the prior orientation.

8. The medical system according to claim 1, wherein the ultrasound probe comprises:
   an ultrasound sensor;
   an elongated shaft; and
   a wrist mechanism coupling the ultrasound sensor to the elongated shaft so as to allow pitch and yaw movement of the ultrasound sensor relative to an axis running along a length of the elongated shaft.

9. A method implemented in a medical system having a first robotic arm mechanically coupled to an ultrasound probe that is disposed at a current location, the medical system further having a display and a processor, the method comprising: displaying a first clickable thumbnail and a second clickable thumbnail on the display, the first clickable thumbnail appearing on the display as a first ultrasound image slice of an object previously captured by the ultrasound probe while at a first location, the second clickable thumbnail appearing on the display as a second ultrasound image slice of the object previously captured by the ultrasound probe while at a second location; conditioned upon a user clicking on the first clickable thumbnail: the processor automatically commanding the first robotic arm to move the ultrasound probe from a current location to the first location; after commanding the first robotic arm to automatically move the ultrasound probe from the current position to the first location and conditioned upon receiving a command associated with a first trajectory of positions, the processor commanding the first robotic arm to automatically move the ultrasound probe along the first trajectory of positions; and conditioned upon the user clicking on the second clickable thumbnail: the processor automatically commanding the first robotic arm to move the ultrasound probe from the current location to the second location.

10. The method according to claim 9, wherein the first trajectory of positions comprises a plurality of positions that follow a contour of the object.

11. The method according to claim 9, wherein the command associated with the first trajectory is a voice command.

12. The method according to claim 9, wherein the command associated with the first trajectory derives from a selection indicated by an option provided in a graphical user interface.

13. The method according to claim 9, wherein the command associated with the first trajectory derives from a selection indicated by a switch position.

14. The method according to claim 9, wherein the first robotic arm includes a joint, and wherein the first location is identified by using information of a position of the joint when the ultrasound probe was previously at the first location.

15. The method according to claim 9, wherein the ultrasound probe was at a prior orientation when the ultrasound probe was previously at the first location, and the method further comprising:
conditioned upon the user clicking on the first clickable thumbnail:
the processor automatically commanding the first robotic arm to orient the ultrasound probe to the prior orientation.

16. The method according to claim 9, wherein the ultrasound probe comprises:
an ultrasound sensor;
an elongated shaft; and
a wrist mechanism coupling the ultrasound sensor to the elongated shaft so as to allow pitch and yaw movement of the ultrasound sensor relative to an axis running along a length of the elongated shaft.

* * * * *

UNITED STATES PATENT AND TRADEMARK OFFICE
CERTIFICATE OF CORRECTION

PATENT NO.       : 10,646,293 B2
APPLICATION NO.  : 15/413380
DATED            : May 12, 2020
INVENTOR(S)      : Christopher J. Hasser et al.

Page 1 of 1

It is certified that error appears in the above-identified patent and that said Letters Patent is hereby corrected as shown below:

In the Specification

Column 1, Lines 14 to 17, replace the paragraph with the following:
--This invention was made with government support under RR019159 and CA103468 awarded by the National Institutes of Health and 9731748 awarded by the National Science Foundation. The government has certain rights in the invention.--

Signed and Sealed this
Eighth Day of September, 2020

Andrei Iancu
*Director of the United States Patent and Trademark Office*